(12) United States Patent
Batra et al.

(10) Patent No.: US 7,702,104 B2
(45) Date of Patent: Apr. 20, 2010

(54) SYSTEM AND METHOD FOR SECURING GENOMIC INFORMATION

(75) Inventors: Virinder Mohan Batra, Chapel Hill, NC (US); Mine Altunay, Raleigh, NC (US); Chetna Dnyandeo Warade, Arlington, MA (US); Daniel Colonnese, Durham, NC (US); Lindsay Kathleen Wilber, Charlottesville, VA (US); Satyaprasad Vadlamudi, Chapel Hill, NC (US)

(73) Assignee: International Business Machines Corporation, Armonk, NY (US)

( * ) Notice: Subject to any disclaimer, the term of this patent is extended or adjusted under 35 U.S.C. 154(b) by 358 days.

(21) Appl. No.: 10/816,393

(22) Filed: Apr. 1, 2004

(65) Prior Publication Data

US 2005/0234655 A1 Oct. 20, 2005

(51) Int. Cl.
*H04K 1/00* (2006.01)
*H04L 9/00* (2006.01)

(52) U.S. Cl. .................... 380/255; 705/50; 706/13; 707/3; 211/41.12; 702/20

(58) Field of Classification Search ............... None
See application file for complete search history.

(56) References Cited

U.S. PATENT DOCUMENTS 6,531,316 B1 * 3/2003 Patten et al. ............. 435/455
6,606,622 B1 8/2003 Sorace et al.

2003/0055835 A1 3/2003 Roth
2004/0221163 A1 * 11/2004 Jorgensen et al. ........... 713/182

OTHER PUBLICATIONS

"Encrypt" definition, Merriam-Webster online dictionary, 2007, on the world wide web at http://mw1.merriam-webster.com/dictionary/encrypt, 2 pages.*
"Encipher" definition, Merriam-Webster online dictionary, 2007, on the world wide web at http://mw1.merriam-webster.com/dictionary/encipher, 2 pages.*
"Encode" definition, Merriam-Webster online dictionary, 2007, on the world wide web at http://mw1.merriam-webster.com/dictionary/encode, 2 pages.*
"Cipher" definition, Merriam-Webster online dictionary, 2007, on the world wide web at http://mw1.merriam-webster.com/dictionary/cipher, 2 pages.*
http://www.bioinformaticsworld.info/feature3b.html, "The Grid: From Concept to Reality in Distributed Computing," downloaded Aug. 29, 2003, 8 pages.
Critchlow, T., "Report on XEWA-00: The XML Enabled Wide-Area Searches for Bioinformatics Workshop," SIDMOD Record, vol. 30, No. 1, Mar. 2001, pp. 58-61.
Rungsarityotin, W., et al., "Grid Computing and Bioinfomiatics Development: A Case Study on the *Oryza saliva* (rice) Genome," Pure Applied Chemistry, vol. 74, No. 6, 2002 IUPAC, pp. 891-897.

* cited by examiner

*Primary Examiner*—Carolyn L. Smith
(74) *Attorney, Agent, or Firm*—Andrea Bauer; Hoffman Warnick LLC

(57) ABSTRACT

A system and method for securing an electronic transmission of a nucleotide chain. A security system is provided that comprises: a system for identifying coding and non-coding regions in the nucleotide chain; and a system for selectively encrypting only the coding regions identified in the nucleotide chain.

16 Claims, 3 Drawing Sheets

SYSTEM AND METHOD FOR SECURING GENOMIC INFORMATION

BACKGROUND OF THE INVENTION

1. Technical Field

The present invention relates to securing genomic information, and more specifically relates to a system and method for selectively securing genetic coding regions being communicated over a network using web services.

2. Related Art

Grid computing (or the use of a computational grid) is a term of art for applying the resources of many computers in a network to a single problem at the same time—usually to a scientific or technical problem that requires a great number of computer processing cycles or access to large amounts of data.

In one important application, grid computing technologies enable the sharing of bioinformatics data from different sites by creating a virtual organization of the data. Specifically, bioinformatics grids allow the sharing of geographically distributed bioinformatics data. Thus, genetic research results can be stored on a local system and shared with the research community immediately. Moreover, users no longer need to know the location of their target information, but are able to access and retrieve data in a transparent manner. This paradigm is extremely appropriate for many types of bioinformatics research efforts, including large-scale genomic and proteomic activities.

Grid technologies are feasible thanks in part to a standardized network technology referred to as web services. Web services (sometimes called application services) are network services that are made available from an application server for web users or other web-connected programs. The use of web services is a major web trend for communicating data and services on the Internet. Because web services can be implemented on a peer-to-peer basis, and not just on a central server, it lends itself to grid computing.

Standardized data exchange within web services is enabled with the use of Extensible Markup Language (XML) documents. In a typical bioinformatics application, XML documents are utilized to hold important information, such as nucleotide chains and the identification of genetic sequences, which are communicated remotely to the computational grid.

While the use of web services and computational grids provide numerous advantages when applied to bioinformatics, there are several challenges that remain. One of the challenges with using web services for bioinformatics relates to security. Existing secure web service standards only provide encryption mechanisms for either specific attributes of the XML message, or the entire XML message. However, because nucleotide chains are very large, e.g., it is not unusual for a chain to comprise many megabytes, encrypting and decrypting the entire chain requires a significant amount of computational time. For example, the magnaporthe grisea genome has approximately 40 millions basepairs, and the length of a human genome is approximately 3,000 million basepairs. Accordingly, a need exists for a system for handling and selectively securing regions of bioinformatics sequences being transmitted and processed in a web services environment.

SUMMARY OF THE INVENTION

The present invention addresses the above-mentioned problems, as well as others, by providing a system and method for providing security to a nucleotide chain over a network by encrypting only selected regions of the chain. In a first aspect, the invention provides a security system for securing an electronic transmission of a nucleotide chain, comprising: a system for identifying coding and non-coding regions in the nucleotide chain; and a system for selectively encrypting only the coding regions identified in the nucleotide chain.

In a second aspect, the invention provides a method for securely transmitting a nucleotide chain, comprising: identifying coding and non-coding regions in the nucleotide chain; selectively encrypting only the coding regions identified in the nucleotide chain to generate encrypted coding regions and unencrypted non-coding regions; and transmitting the encrypted coding regions and unencrypted non-coding regions.

In a third aspect, the invention provides a program product stored on a recordable medium for encoding a nucleotide chain, comprising: means for identifying coding and non-coding regions in the nucleotide chain; and means for selectively encrypting only the coding regions identified in the nucleotide chain.

In a fourth aspect, the invention provides a program product stored on a recordable medium for decoding an encoded nucleotide chain, comprising: means for identifying coding and non-coding regions in the encoded nucleotide chain; means for selectively decrypting only the coding regions identified in the encoded nucleotide chain; and means for reassembling the coding and non-coding regions to generate a decoded nucleotide chain.

BRIEF DESCRIPTION OF THE DRAWINGS

These and other features of this invention will be more readily understood from the following detailed description of the various aspects of the invention taken in conjunction with the accompanying drawings in which.

DETAILED DESCRIPTION OF THE INVENTION

Figure 1:
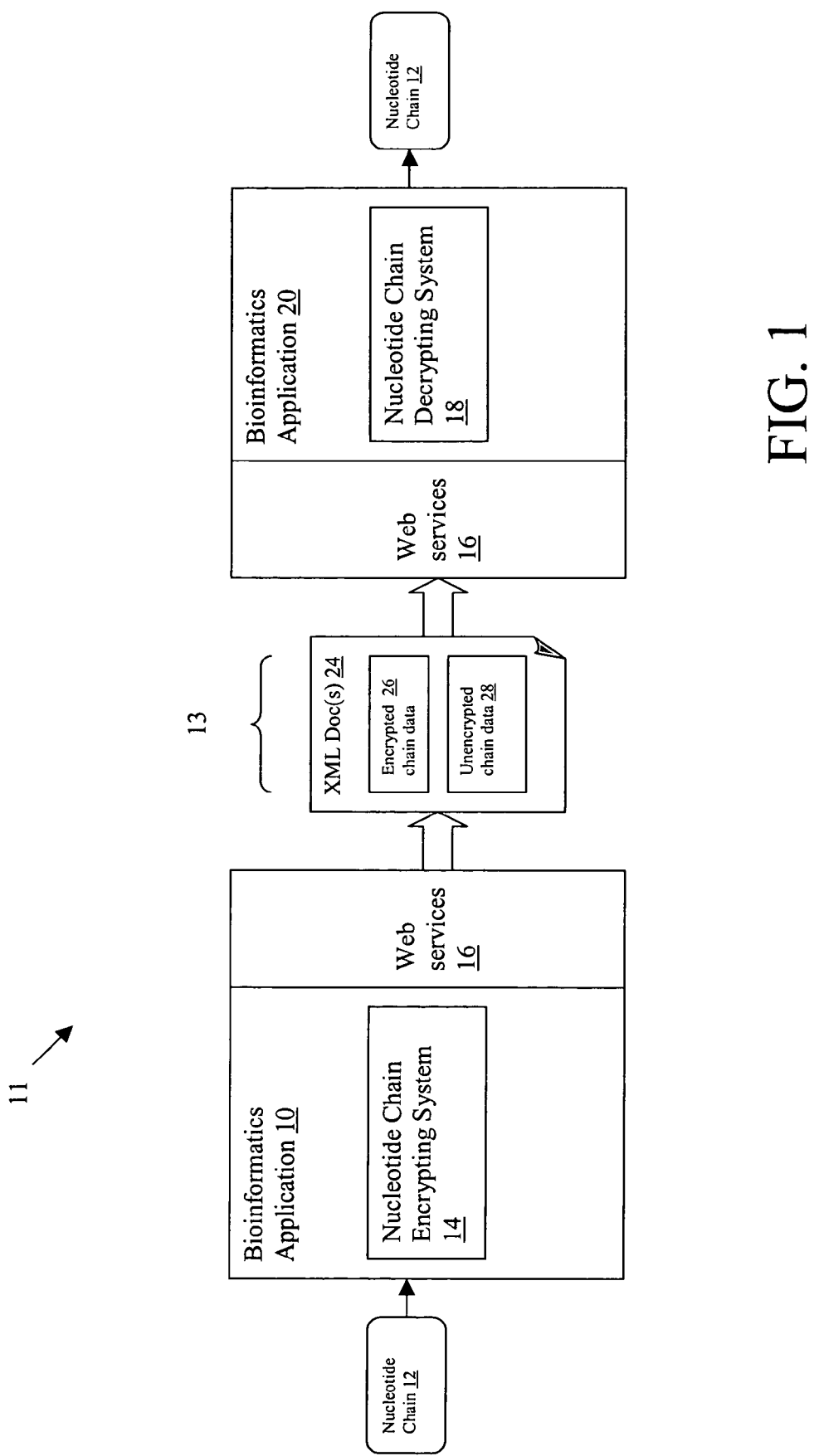
FIG. 1 depicts a bioinformatics system for securely communicating an encoded nucleotide chain in accordance with the present invention.

Referring now to the drawings, FIG. 1 depicts a bioinformatics system 11 for communicating an encoded nucleotide chain 12 from a first application 10 to a second application 20. In one exemplary embodiment, applications 10 and 20 provide a query or search system wherein application 10 provides a remote application for inputting a nucleotide chain query, and application 20 provides a bioinformatics database, which can be queried with the inputted nucleotide chain. In other possible embodiments, applications 10 and 20 may represent any two systems that communicate bioinformatics data, for example, applications 10 and 20 may represent nodes within a computational grid, a system for uploading bioinformatics information to a database, a client and server, two servers, email applications, etc.

In the embodiment depicted in FIG. 1, data transfer between applications 10 and 20 is implemented using web services 16, which utilizes one or more XML documents 24 to transmit the encoded nucleotide chain 13. Application 10 includes a nucleotide chain encrypting system 14 for encrypting portions of chain 12, and application 20 includes a decrypting system 18 for decrypting an encoded chain 13.

Obviously, either or both applications 10 and 20 may include both an encrypting and a decrypting system to facilitate secure bi-directional data transfers.

As noted above, encrypting an entire nucleotide chain can be a computationally intensive process. To address this, the present invention encrypts only selected coding regions of the nucleotide chain 12. Coding regions, i.e., exons, are the only part of a nucleotide chain that convey information about the genome being studied. The non-coding regions or introns, represent junk DNA that do not convey information about the genome. In accordance with the present invention, the non-coding regions are not encrypted, thereby greatly reducing the computational requirements of bioinformatics system 11. As shown in FIG. 1, an encoded chain 13 is generated using XML document(s) 24 comprising encrypted chain data 26 (comprised of coding regions) and unencrypted chain data 28 (comprised of non-coding chain data).

Figure 2:
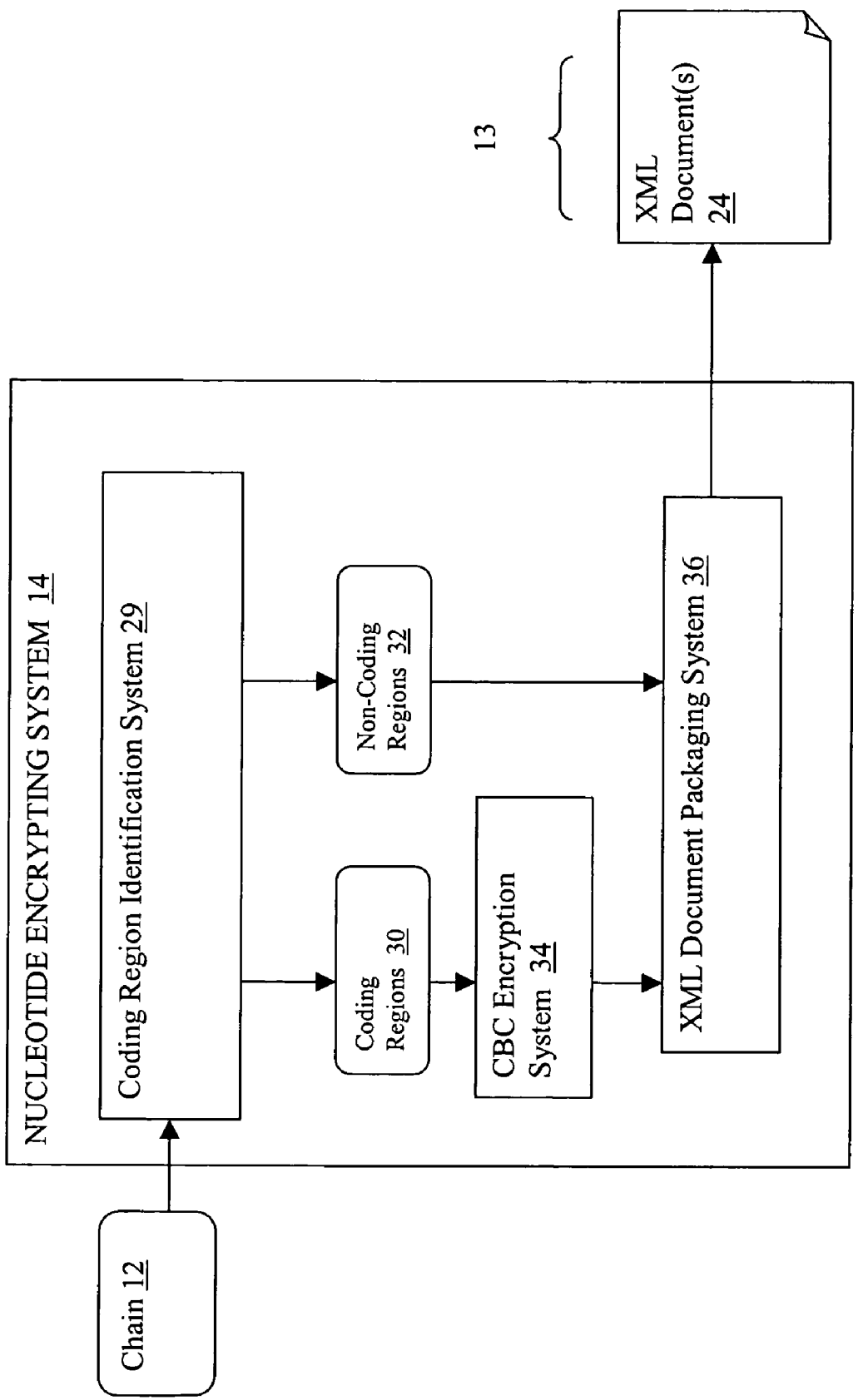
FIG. 2 depicts an encrypting system in accordance with the present invention.
Figure 3:
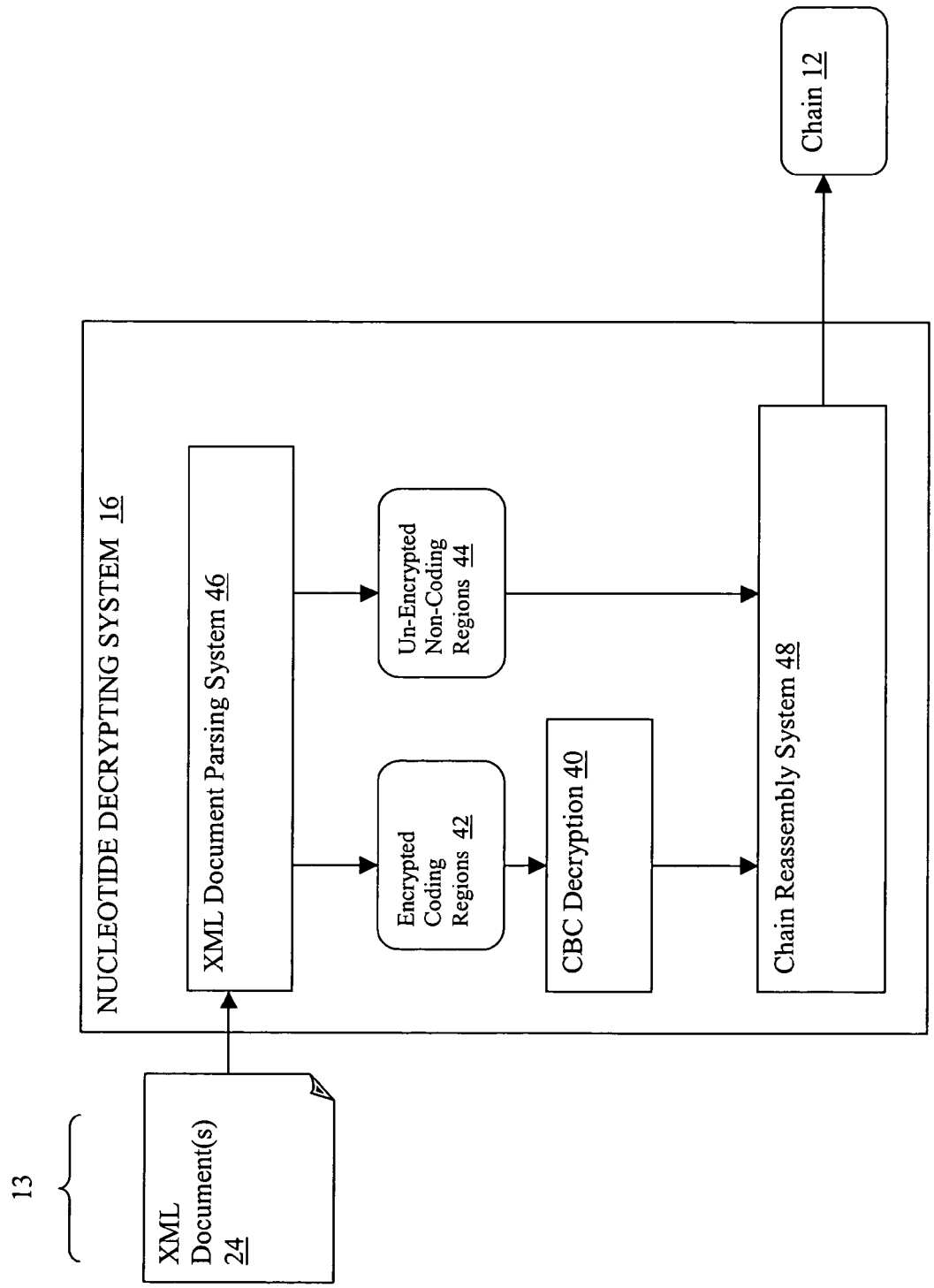
FIG. 3 depicts a decrypting system in accordance with the present invention.

Referring now to FIGS. 2 and 3, exemplary embodiments of nucleotide chain encrypting system 14 and nucleotide chain decrypting system 16 are described in further detail. As shown in FIG. 2, nucleotide chain encrypting system 14 includes a coding region identification system 29 that receives a nucleotide chain 12 and identifies the coding regions 30 and non-coding regions 32 in the chain 12. Systems for handling this process are well known in the art, and are therefore not explained in further detail herein. Coding region identification system 30 splits nucleotide chain 12 into "islands" of coding and non-coding regions 30, 32, e.g.,

[non-coding region] [coding region] [non-coding region] [coding region] . . .

The coding regions 30 are encrypted, in this case, using cipher block chain (CBC) encryption system 34. CBC is known encryption technique that encrypts a sequence of bits as a single unit, or block, with a cipher key. CBC uses a chaining mechanism that allows the decryption of a block of ciphertext to depend on all the preceding ciphertext blocks. Thus, the validity of a block is contained in the immediately previous cipertext block. Accordingly, the validity of each coding region can be proved by the immediately preceding coding region. While CBC is a particularly robust solution for this type of application, it should be recognized that any encryption, encoding, or security technique could be utilized to secure the coding regions 30, and thus fall within the scope of this invention.

XML document packaging system 36 receives the encrypted coding regions 30 and unencrypted non-coding regions 32, and "packages" the regions in one or more XML documents 24. The regions can be packaged in any manner, e.g., each region could be stored into a unique XML document; multiple regions could be stored in a single XML document; multiple regions could be stored in multiple XML documents, etc. It should be understood that nucleotide chain encrypting system 14 describes one exemplary embodiment for encrypting and packaging coding and non-coding regions 30, 32, and that other embodiments are possible and fall within the scope of the invention. For instance, nucleotide chain encrypting system 14 could package the regions 30, 32 into one or more XML documents before the coding regions 30 are encrypted.

The following is an exemplary XML document containing coding and non-coding regions of a simplified nucleotide sequence:

SEQ ID NO: 1 CGATCCAA . . . CAGAGTCCAGGAC-CCAA . . . ATGAAACGTCCATT wherein the bolded nucleotides indicate coding regions, and ". . ." indicates nucleotides omitted for brevity purposes.

```
*****************
<XML doc>doc 1</XML doc>
<Sequence Name>Nuc Seq 1</Sequence Name>
    <non-coding_region.1>CGATCCAA...CAG</non-coding_region.1>
    <coding_region.1>AGTCCA</coding_region.1>
    <non-coding_region.2>GGACCCAA...ATG</non-coding_region.2>
    <coding_region.2>AAACGTCCATT</coding_region.2>
*****************
```

In the above example, coding_region.1 (nucleotides 12-17 of SEQ ID NO:1). and coding_region.2 (nucleotides 29-39 of SEQ ID NO: 1). are encrypted to secure the exact coding sequences that convey information about the genome being studied. As noted, using CBC, the validity of coding_region.2 can be proved based on coding_region.1. Non-coding_region.1 (nucleotides 1-11 of SEQ ID NO: 1). and non-coding_13 region. 2(nucleotides 18-28 of SEQ ID NO: 1) are not encrypted since they do not convey any relevant information. Obviously, the exact format (e.g., tag names, etc.) of XML document(s) 24 can be implemented in any workable/desirable manner.

Referring to FIG. 3, nucleotide chain decrypting system 16 is shown, which is used to regenerate nucleotide chain 12 from XML document(s) 24. Nucleotide decrypting system 16 includes an XML document parsing system 46, which identifies the encrypted coding regions 42 and unencrypted coding regions 44. Encrypted coding regions 42 are subsequently decrypted by CBC decryption system 40. Once decrypted, chain reassembly system 48 reassembles the regions back to the original nucleotide chain 12.

It is understood that the systems, functions, mechanisms, methods, engines and modules described herein can be implemented in hardware, software, or a combination of hardware and software. They may be implemented by any type of computer system or other apparatus adapted for carrying out the methods described herein. A typical combination of hardware and software could be a general-purpose computer system with a computer program that, when loaded and executed, controls the computer system such that it carries out the methods described herein. Alternatively, a specific use computer, containing specialized hardware for carrying out one or more of the functional tasks of the invention could be utilized. The present invention can also be embedded in a computer program product, which comprises all the features enabling the implementation of the methods and functions described herein, and which—when loaded in a computer system—is able to carry out these methods and functions. Computer program, software program, program, program product, or software, in the present context mean any expression, in any language, code or notation, of a set of instructions intended to cause a system having an information processing capability to perform a particular function either directly or after either or both of the following: (a) conversion to another language, code or notation; and/or (b) reproduction in a different material form.

The foregoing description of the invention has been presented for purposes of illustration and description. It is not intended to be exhaustive or to limit the invention to the precise form disclosed, and obviously, many modifications and variations are possible. For instance, while the present invention has been described with reference to a system utilizing XML documents, the concepts and techniques could be applied to any system for communicating electronic data. Such modifications and variations that may be apparent to a person skilled in the art are intended to be included within the scope of this invention as defined by the accompanying claims.

---

---

The invention claimed is:

1. A computer-implemented security system for securing an electronic version of a nucleotide chain sequence, wherein the nucleotide chain sequence comprises at least a portion of a genome of an organism, the system comprising:
   a computer hardware apparatus; and
   a computer program that, when loaded and executed, controls the computer hardware apparatus such that it carries out:
   on a first application,
      identifying a sequence of at least one exon and a sequence of at least one intron in the nucleotide chain sequence;
      selectively encrypting the sequence of only the at least one exon identified in the nucleotide chain to provide security over a network, wherein the selectively encrypting only the sequence of the at least one exon utilizes cipher block chain encrypting;
      outputting the electronic version of the nucleotide chain sequence, including both the encrypted sequence of the at least one exon and the unencrypted sequence of the at least one intron,
      wherein the outputting includes transmitting the encrypted sequence of the at least one exon and the unencrypted sequence of the at least one intron; and
   on a second application,
      receiving the encrypted sequence of the at least one exon and the unencrypted sequence of the at least one intron;
      decrypting the encrypted sequence of the at least one exon; and
      regenerating the nucleotide chain from the decrypted sequence of the at least one exon and the unencrypted sequence of the at least one intron to re-form the original nucleotide chain sequence.

2. The computer-implemented security system of claim 1, wherein the transmitting includes packaging the encrypted sequence of the at least one exon and the unencrypted sequence of the at least one intron into at least one XML document.

3. The computer-implemented security system of claim 1, wherein the transmitting of the encrypted sequence of the at least one exon and the sequence of the at least one unencrypted intron utilizes web services.

4. The computer-implemented security system of claim 1, wherein the receiving comprises receiving the encrypted sequence of the at least one exon and the unencrypted sequence of the at least one intron into a bioinformatics database for receiving nucleotide chain queries.

5. A computer implemented method for transmitting a nucleotide chain sequence, wherein the nucleotide chain sequence comprises at least a portion of a genome of an organism, the method comprising:
   on a computer hardware apparatus,
      identifying a sequence of at least one exon and a sequence of at least one intron in the nucleotide chain sequence;
      selectively encrypting the sequence of only the at least one exon identified in the nucleotide chain, wherein the selectively encrypting only the sequence of the at least one exon utilizes cipher block chain encrypting;
      transmitting the encrypted sequence of the at least one exon and the unencrypted sequence of the at least one intron;
      receiving the encrypted sequence of the at least one exon and the unencrypted sequence of the at least one intron;
      decrypting the encrypted sequence of the at least one exon;
      regenerating the nucleotide chain sequence from the decrypted sequence of the at least one exon and unencrypted sequence of the at least one intron to re-form the original nucleotide chain sequence; and
      outputting the regenerated nucleotide chain sequence.

6. The method of claim 5, comprising the further step of querying a bioinformatics database with the received nucleotide chain sequence.

7. The method of claim 5, wherein the encrypted sequence of the at least one exon and the unencrypted sequence of the at least one intron are transmitted in at least one XML document.

8. The method of claim 5, wherein the encrypted sequence of the at least one exon and the unencrypted sequence of the at least one intron are transmitted using web services.

9. A program product stored on a recordable storage medium comprising instructions executable by a computer system that when executed, cause the computer system to implement a method encoding a nucleotide chain sequence, wherein the nucleotide chain sequence comprises at least a portion of a genome of an organism, the method comprising:

identifying a sequence of at least one exon and a sequence of at least one intron in the nucleotide chain sequence;

selectively encrypting only the sequence of the at least one exon identified in the nucleotide chain sequence to provide security over a network, wherein the selectively encrypting includes utilizing cipher block chain encrypting; and outputting the nucleotide chain sequence including both the encrypted sequence of the at least one exon and the unencrypted sequence of the at least one intron over the network, the outputting including transmitting the encrypted sequence of the at least one exon and the unencrypted sequence of the at least one intron;

receiving the encrypted sequence of the at least one exon and the unencrypted sequence of the at least one intron;

decrypting the encrypted sequence of the at least one exon; and regenerating the nucleotide chain from the decrypted sequence of the at least one exon and the unencrypted sequence of the at least one intron to re-form the original nucleotide chain sequence.

10. The program product of claim 9, wherein the encrypted sequence of the at least one exon and unencrypted sequence of the at least one intron are stored in at least one XML document.

11. A program product stored on a recordable storage medium comprising instructions executable by a computer system that when executed, cause the computer system to implement a method for decrypting an encrypted nucleotide chain, wherein the nucleotide chain sequence comprises at least a portion of a genome of an organism, the method comprising:

identifying an encrypted sequence of at least one exon and an unencrypted sequence of at least one intron in the nucleotide chain sequence;

selectively decrypting only the encrypted sequence of the at least one exon identified in the nucleotide chain sequence, wherein the sequence of the at least one exon is encrypted using cipher block chain encryption;

reassembling the sequence of the at least one exon and the sequence of the at least one intron to generate a decrypted nucleotide chain sequence; and outputting the decrypted nucleotide chain sequence.

12. The program product of claim 11, wherein the sequence of the at least one exon and the sequence of the at least one intron are stored in at least one XML document.

13. The program product of claim 11, further comprising querying a bioinformatics database with the decrypted nucleotide chain sequence.

14. The computer-implemented security system of claim 2, wherein the packaging occurs prior to selectively encrypting the sequence of only the at least one exon identified in the nucleotide chain.

15. The computer-implemented security system of claim 2, wherein the packaging includes packaging the sequence of the at least one exon in a first unique XML document and packaging the sequence of the at least one intron in a second unique XML document.

16. The method of claim 7, wherein the encrypted sequence of the at least one exon and the unencrypted sequence of the at least one intron are packaged into the at least one XML document prior to selectively encrypting the sequence of only the at least one exon identified in the nucleotide chain.

* * * * *

SEQUENCE LISTING

<160> NUMBER OF SEQ ID NOS: 1

<210> SEQ ID NO 1
<211> LENGTH: 39
<212> TYPE: DNA
<213> ORGANISM: Artificial Sequence
<220> FEATURE:
<223> OTHER INFORMATION: Arbitrary DNA sequence used for demonstrative
      purposes

<400> SEQUENCE: 1

```
cgatccaaca g agt cca ggacccaaat g aaa cgt cca tt                      39
            Ser Pro           Lys Arg Pro
            1                 5
```